United States Patent [19]

Zaccardi

[11] Patent Number: 5,536,660
[45] Date of Patent: Jul. 16, 1996

[54] STREPTOMYCES VIRIDODIASTATICUS SUBSP. "LITTUS" NRRL-21082N CAPABLE OF PRODUCING ANTIBIOTICS

[75] Inventor: Joseph A. Zaccardi, New Windsor, N.Y.

[73] Assignee: American Cyanamid Company, Madison, N.J.

[21] Appl. No.: 432,490

[22] Filed: May 1, 1995

Related U.S. Application Data

[62] Division of Ser. No. 150,639, Nov. 10, 1993, Pat. No. 5,426,108.

[51] Int. Cl.$^6$ .................... C12N 1/00; C12N 1/20
[52] U.S. Cl. .............. 435/253.5; 435/132; 435/170; 435/886; 514/250
[58] Field of Search .................. 435/253.5, 132, 435/170, 886; 514/250; 544/341

[56] References Cited

U.S. PATENT DOCUMENTS

| | | | |
|---|---|---|---|
| 4,003,902 | 1/1977 | Kluepfel et al. | 260/268 |
| 4,686,308 | 8/1987 | Umezawa et al. | 364/219 |
| 4,992,551 | 2/1991 | Saito et al. | 544/342 |
| 5,426,108 | 6/1995 | Zaccardi | 514/250 |

OTHER PUBLICATIONS

ATCC, Catalogue of Bact. & Bacteriophages, 18th ed., pp. 357–358, 1992.

Primary Examiner—David M. Naff
Assistant Examiner—Deborah K. Ware
Attorney, Agent, or Firm—Steven R. Eck

[57] ABSTRACT

This invention relates to antibiotics $31F508\alpha_1$, $31F508\alpha_2$, $31F508\beta_1$ and $31F508\beta_2$, produced by the microorganism *Streptomyces viridodiastaticus* subsp. "littus" NRRL-2108211. The antibiotics are useful as antibacterial agents against gram-positive and gram-negative bacteria.

1 Claim, 9 Drawing Sheets

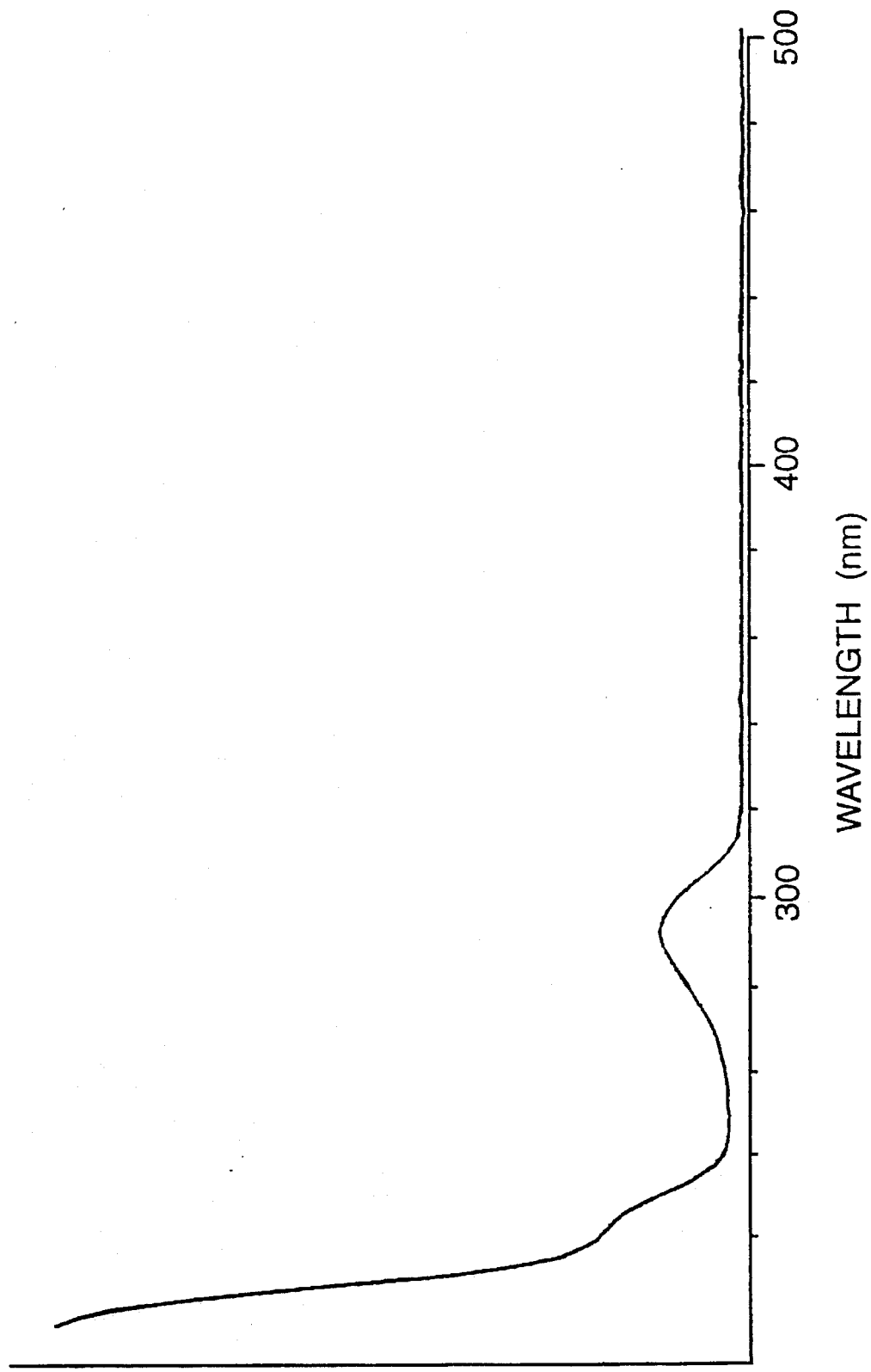

5,536,660

STREPTOMYCES VIRIDODIASTATICUS SUBSP. "LITTUS" NRRL-21082N CAPABLE OF PRODUCING ANTIBIOTICS

This application is a divisional of application Ser. No. 08/150,639, filed Nov. 10, 1993, which is now U.S. Pat. No. 5,426,108.

BACKGROUND OF THE INVENTION

1. Field of the Invention

The invention relates to new antibiotics designated 31F508$\alpha_1$, 31F508$\alpha_2$, 31F508$\beta_1$ and 31F508$\beta_2$, to their production by fermentation, to methods for their recovery and concentration from crude solutions and to processes for their purification. The present invention includes within its scope the agents in dilute form, as crude concentrates, as a complex of all components, in pure form as individual components and a novel strain of *Streptomyces viridodiastaticus* subsp. *"littus"*.

2. Description of the Prior Art

Naphthyridinomycin antibiotics are reported in U.S. Pat. No. 4,003,902.

BRIEF DESCRIPTION OF THE DRAWINGS

FIG. IA, IB shows a proton magnetic resonance spectrum of 31F508$\alpha_1$.

FIG. II shows an ultraviolet absorption spectrum of 31F508$\alpha_2$.

Figure 1A:
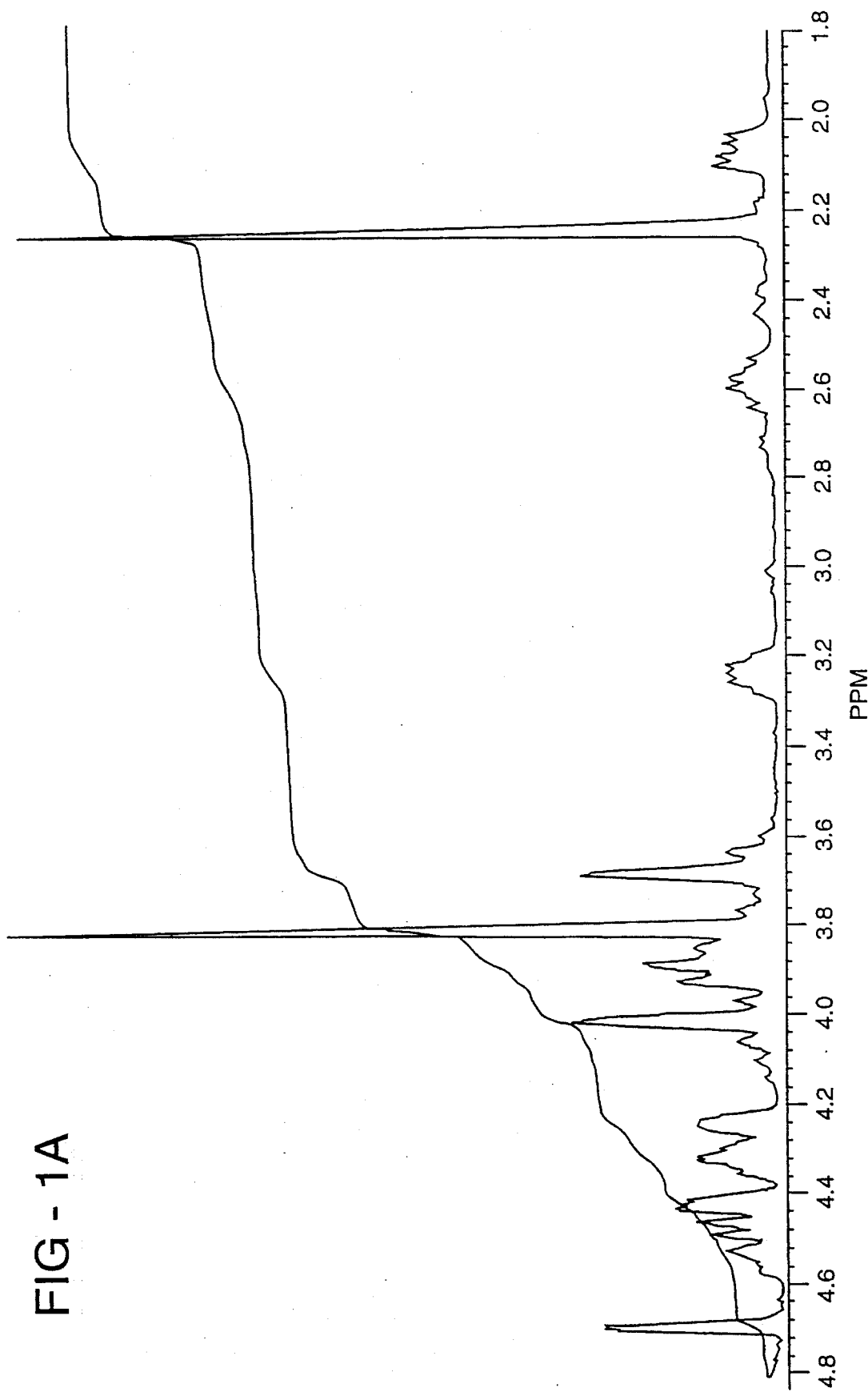
Figure 1B:
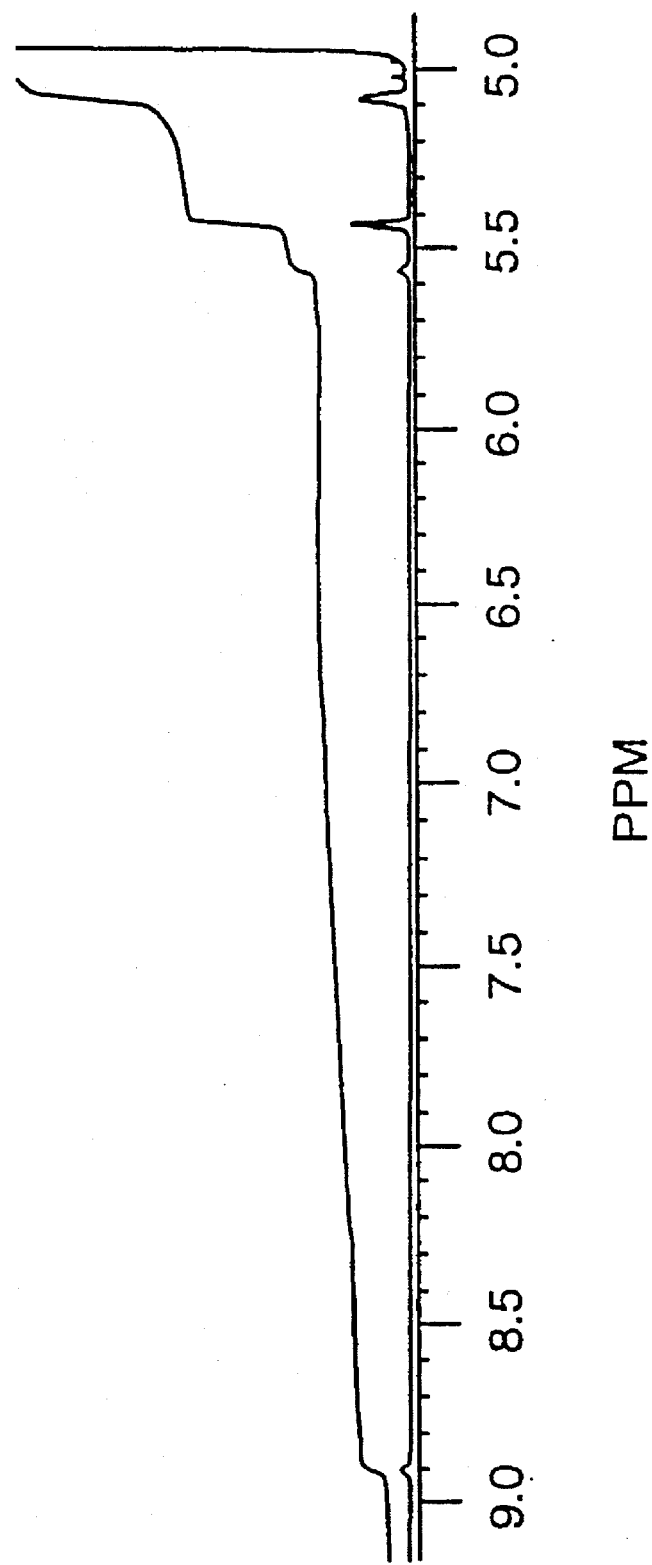
Figure 3:
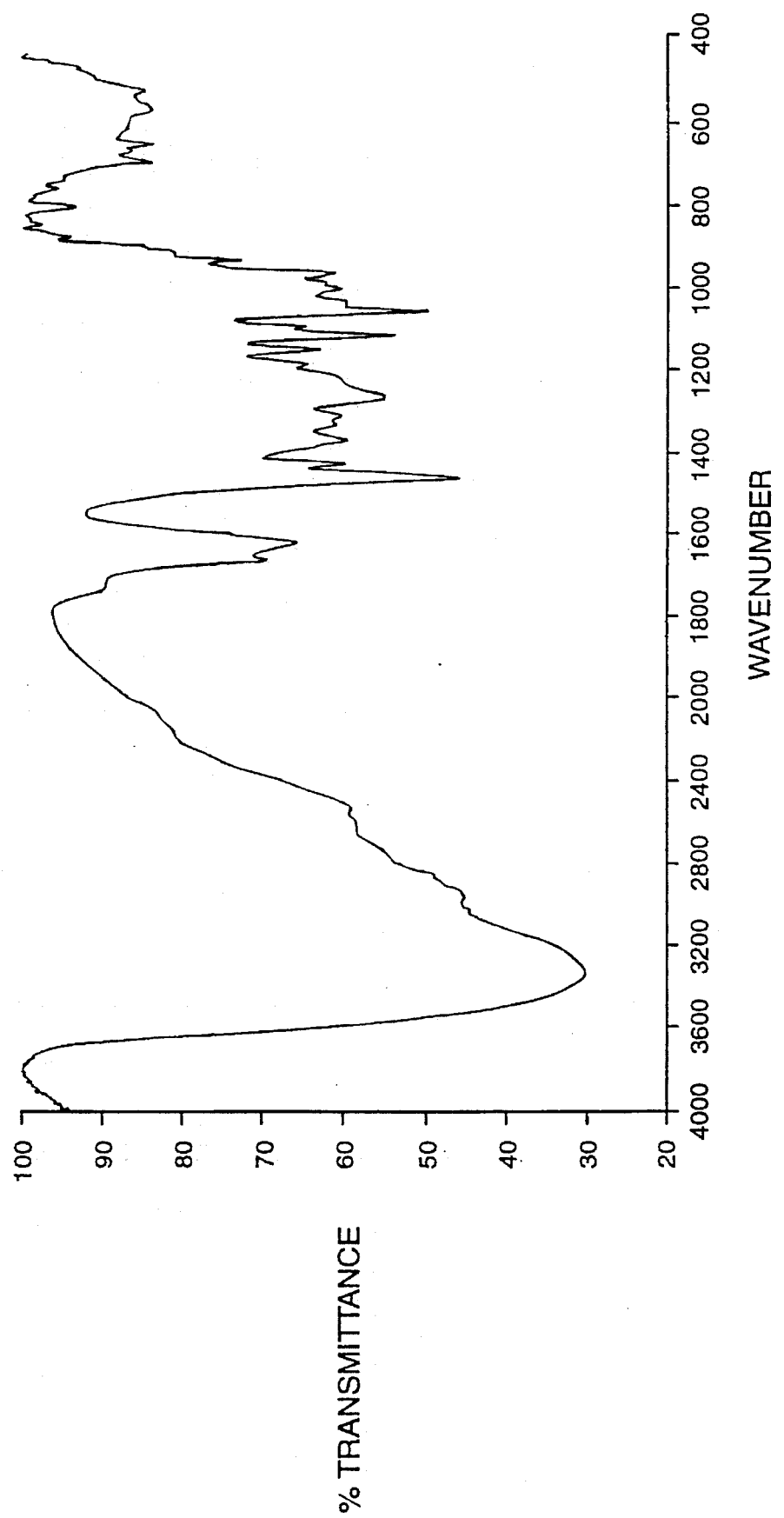
Figure 4:
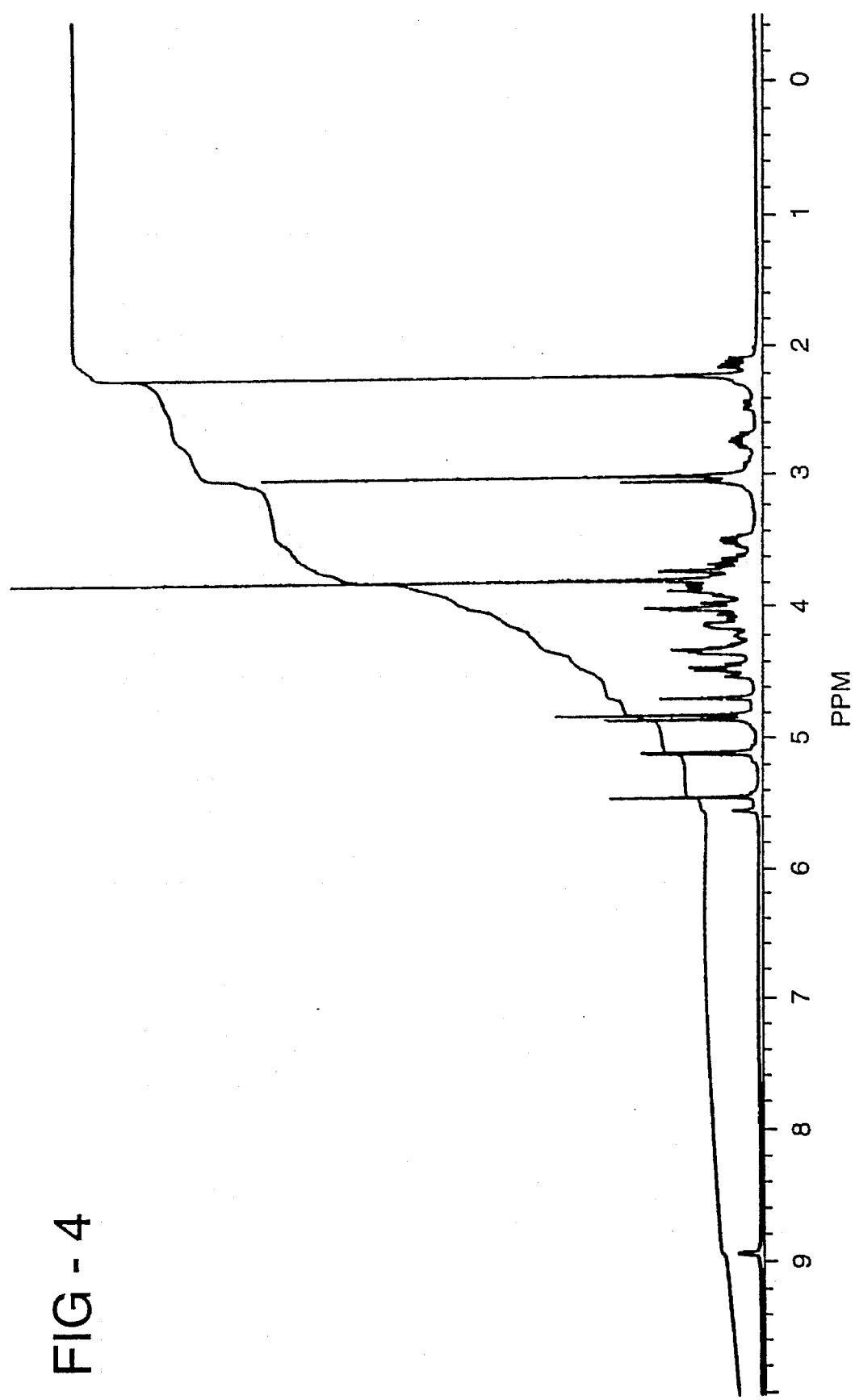
Figure 5:
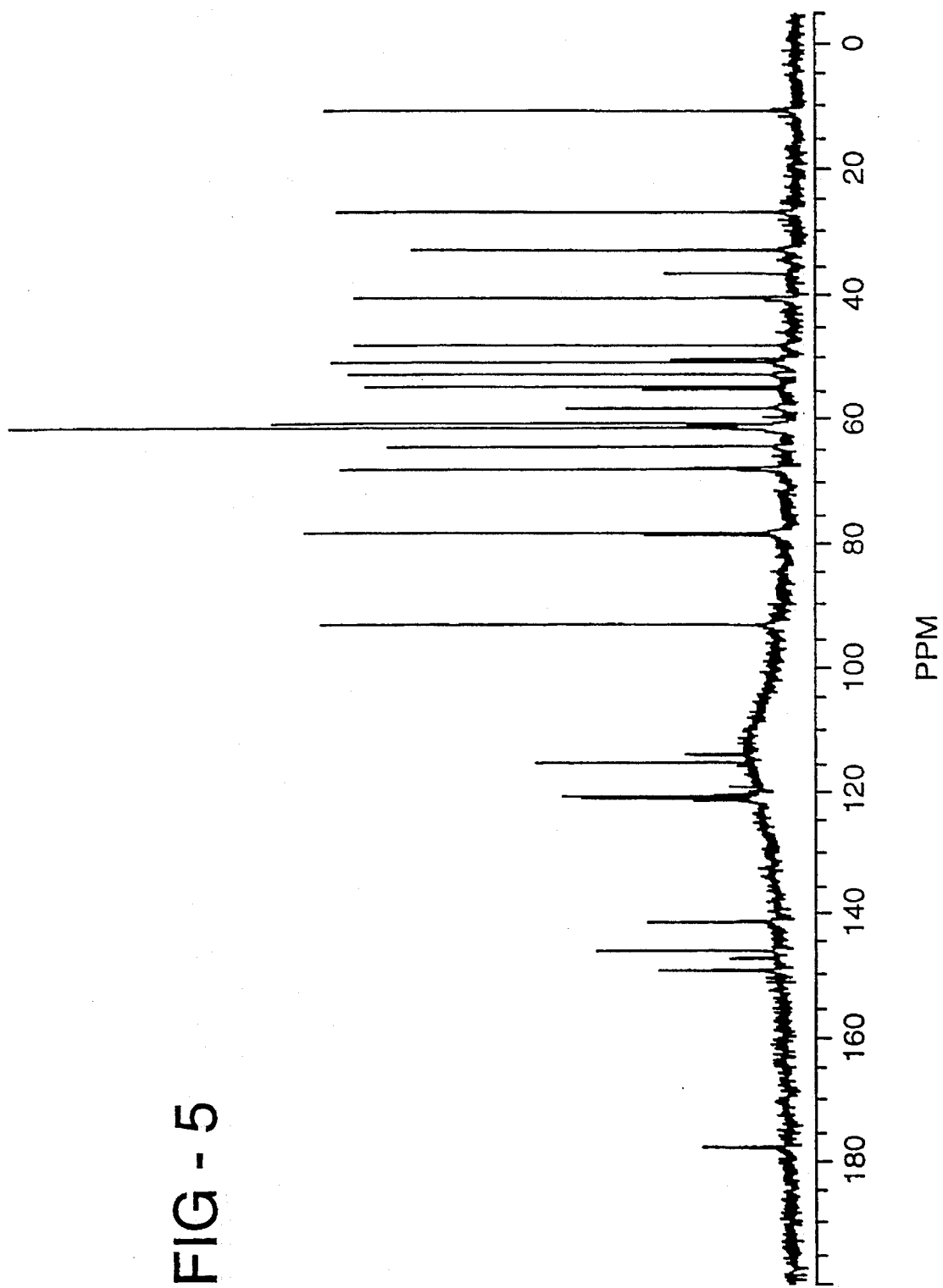
Figure 6:
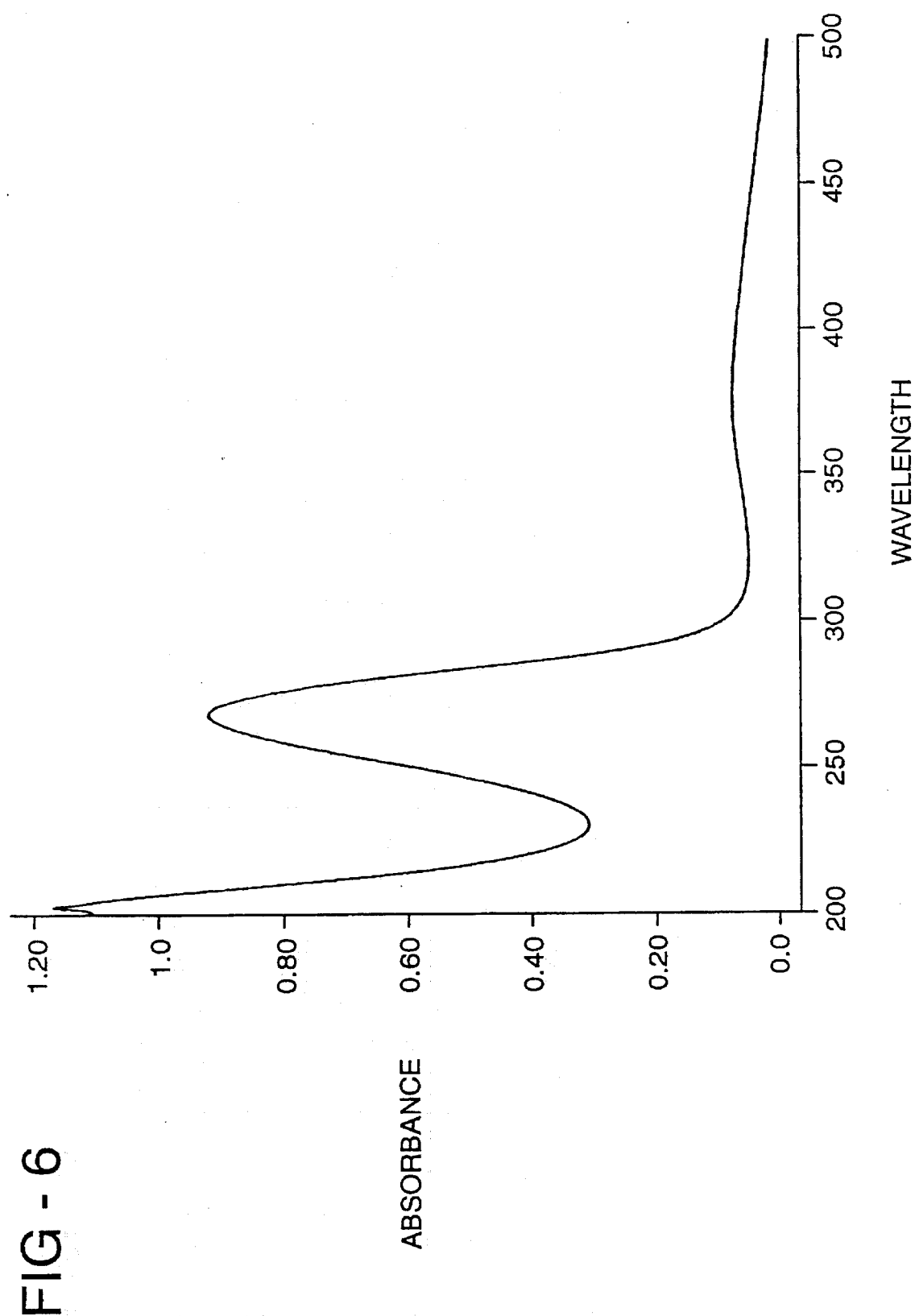
Figure 7:
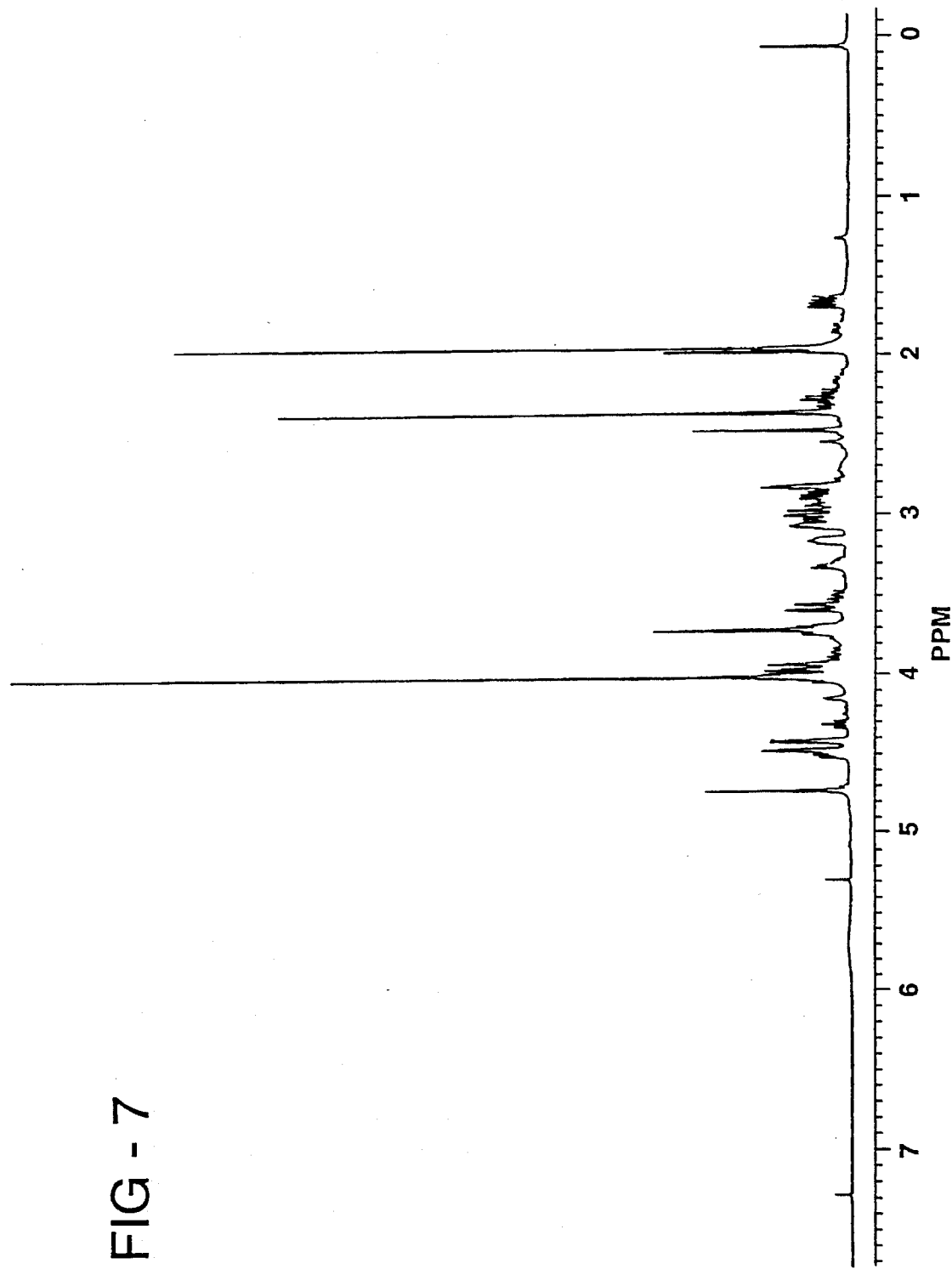
Figure 8:
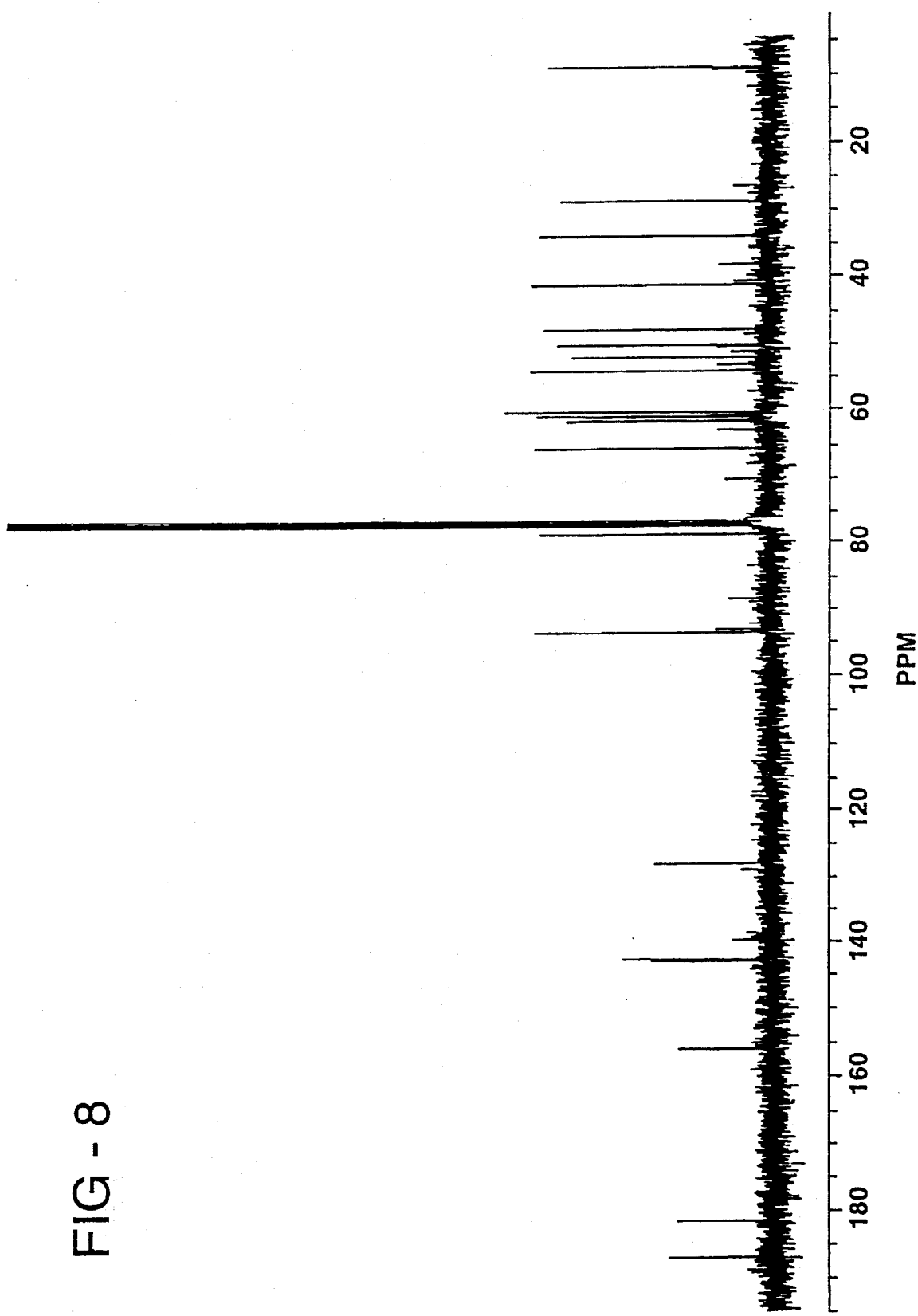

FIG. III shows an infrared absorption spectrum of 31F508$\alpha_2$.

FIG. IV shows a proton magnetic resonance spectrum of 31F508$\alpha_2$.

FIG. V shows a carbon-13 nuclear magnetic resonance spectrum of 31F508$\alpha_2$.

FIG. VI shows a proton magnetic resonance spectrum of 31F508$\beta_2$

FIG. VII shows a proton magnetic resonance spectrum of 31F508$\beta_2$

FIG. VIII shows a carbon-13 nuclear magnetic resonance spectrum

DESCRIPTION OF THE PREFERRED EMBODIMENTS

New antibiotics designated 31F508$\alpha_1$, 31F508$\alpha_2$, 31F508$\alpha_1$ and 31F508$\beta_2$ have not been found. The structure of new antibiotic 31F508$\alpha_1$ is:

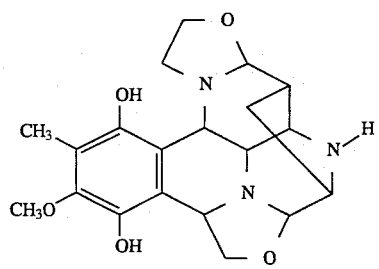

The physico-chemical characteristics of 31F508$\alpha_1$ are as follows:
1F508$\alpha_1$ 1. Molecular weight: 387 (FABMS);

2. Apparent molecular formula:

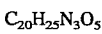

$C_{20}H_{25}N_3O_5$

3. Proton nuclear magnetic resonance spectrum: as shown in FIG. I.

The structure of the new antibiotic 31F508$\alpha_2$ is:

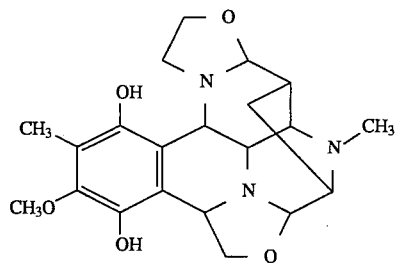

The physico-chemical characteristics of 31F508$\alpha_2$ are as follows:
31F508$\alpha_2$ 1. Molecular weight: 401(FABMS);

2. Apparent molecular formula:

$C_{21}H_{27}N_3O_5$

3. Ultraviolet absorption spectrum: as shown in FIG. II 292NM (n2729) in methyl alcohol.

4. Infrared absorption spectrum as shown in FIG. III (cm$^{-1}$) (KBr disc) 3353, 3026, 2967, 2626, 1662, 1623, 1467, 1429, 1371, 1334, 1270, 1189, 1154, 1120, 1061, 1004, 965, 933.

5. Proton nuclear magnetic resonance spectrum: as shown in FIG. IV (300 MHz, D$_2$O/TFA) ppm 2.08, 2.19 (3H,s), 2.71, 2.95 (3H,s), 3.01, 3.47, 3.62, 3.69, 3.76 (3H,s), 3.831, 3.84, 3.98, 4.1, 4.28, 4.29, 4.43, 4.439, 4.66(1H,s), 4.83 (1H,s), 5.08, 5.43 (1H,s), 5.52.

6. Carbon-13 nuclear magnetic resonance spectrum: as shown in FIG. V (D$_2$O/TFA) ppm 10.06, 26.37, 32.3, 40.02, 47.67, 50.67, 52.47, 54.46, 60.73, 61.54, 61.6, 64.48, 68.11, 78.15, 92.85, 115.03, 120.51, 121.04, 141.09, 145.76, 148.77, 177.49.

The structure of the new antibiotic 31F508$\beta_1$ is:

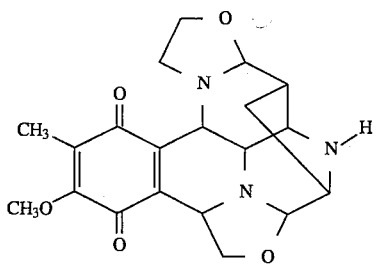

The physico-chemical characteristics of 31F508$\beta_1$ are as follows:
31F508$\beta_1$ 1. Molecular weight: 385(FABMS);

2. Apparent molecular formula:

$C_{20}H_{23}N_3O_5$

The structure of the new antibiotic 31F508b$_2$ is

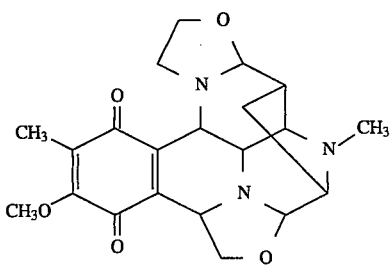

The physico-chemical characteristics of 31F508β$_2$ are as follows: 31F508β$_2$

1. Molecular weight: 399 (FABMS);
2. Apparent molecular formula:

$C_{21}H_{25}N_3O_5$

3. Ultraviolet adsorption spectrum: as shown in FIG. VI. 270NM (n=10508);
4. Proton nuclear magnetic resonance spectrum as shown in FIG. VII. 1.63, 1.94 (3H5), 2.3, 2.35 (3H5), 2.81, 2.95, 3.01, 3.05, 3.15, 3.56, 3.7, 3.72, 3.93, 4.0 (3H5), 4.02, 4.42, 4.73(1H5)
5. Carbon-13 nuclear magnetic resonance spectrum as shown in FIG. VIII. 8.77, 28.69, 33.96, 41.09, 47.87, 50.16, 52.08, 54.24, 60.28, 60.87, 61.71, 65.8, 78.77, 93.62 128.0, 142.59, 142.9, 155.85, 181.48, 186.76

The new antibacterial agents 31F508α$_1$, 31F508α$_2$, 31F508β$_1$ and 31F508β$_2$ are formed during the cultivation under controlled conditions of a new strain of *Streptomyces viridodiastaticus* subsp. "*littus*".

This microorganism is maintained in the culture collection of the Medical Research Division, American Cyanamid Company, Pearl River, N.Y. 10965 as culture 31F508. A viable culture of this new microorganism was deposited on Jul. 23, 1993 with the Patent Culture Collection Laboratory, Northern Regional Research Center, U.S. Department of Agriculture, Peoria, Ill. 61604, and has been added to its permanent collection. It has been assigned the strain designation NRRL-21082N by said depository. Access to said culture, under strain designation NRRL-21082N, during pendency of the instant application, shall be available to one determined by the Commissioner of Patents and Trademarks to be entitled thereto under 37 C.F.R. =1.14 and 35 U.S.C. =122, and all restrictions on availability to the public of such culture will be irrevocably removed upon grant of a patent on the instant application.

Culture 31F508 is isolated from a shoreline soil sample taken from Key West, Fla.

Culture 31F508 has the following cultural characteristics as described and compared to Streptomyces viridodiastaticus for taxonomic identification in Table I.

The macromorphology for culture 31F508 is described and compared to Streptomyces viridodiasticus in Table II.

TABLE I

CULTURAL CHARACTERISITICS

| Characteristic | 31F508 | S. viridodiastaticus |
|---|---|---|
| Aerial Mycelium | Rectiflexibiles | Rectiflexibiles |
| Fragmentation of Substrate Mycelium | None | None |

TABLE I-continued

CULTURAL CHARACTERISITICS

| Characteristic | 31F508 | S. viridodiastaticus |
|---|---|---|
| Zoospores and Sporangia | None | None |
| Spore Chain | 15–20 | 15–20 |
| Spore Shape | Oval | Oval |
| Spore Surface | Spiny | Spiny |
| DAP Analysis | LL-DAP | LL-DAP |

TABLE II

MACROPHORPHOLOGY

| Medium | 31F508 Morphology[a] | S. viridodiastaticus |
|---|---|---|
| Yeast-Malt (ISP2) | G: Abundant | Abundant |
| | AM: Medium Gray (256) | Medium Gray (256) |
| | SM: Gray Yellow-Brown (80,81) | Medium Olive-Brown (95) |
| | SP: None | None |
| Oatmeal (ISP3) | G: Abundant | Abundant |
| | AM: Medium Gray (265) | Medium Gray (265) |
| | SM: Light Olive-Gray (112) | Dark Gray to Dark Yellow (266,88) |
| | SP: None | None |
| Inorganic Salts - Starch (ISP4) | G: Abundant | Abundant |
| | AM: Light to Medium Gray (264,265) | Medium Gray (265) |
| | SM: Medium Gray to Gray Yellow (265,90) | Medium Gray (265) |
| | SP: None | None |
| Glycerol - Asparagine (ISP5) | G: Moderate | Moderate |
| | AM: Medium Gray (265) | Medium Gray (265) |
| | SM: Colorless | Colorless |
| | SP: None | None |

G, growth; AM, aerial mycelium; SM, subtrate mycelium, SP, soluble pigment
[a]ISCC, National Bureau of Standard Centroid Color Charts, Publication 440, Washington, D.C., 1976.

The physiological reactions of 31F508 are shown and compared to Streptomyces viridodiasticus in Table III.

TABLE III

PHYSIOLOGICAL REACTIONS

| | 31F508 | S. viridodiastaticus |
|---|---|---|
| Utilization of Carbon Sources: | | |
| D-Glucose | + | + |
| L-Arabinose | + | + |
| Sucrose | + | + |
| D-Xylose | + | + |
| Inositol | + | + |
| D-Mannitol | + | + |
| β-D-Fructose | + | + |
| α-L-Rhamnose | + | + |
| Raffinose | − | − |
| Cellulose | − | − |
| Hydrolysis of: | | |
| Casein | + | + |
| Xanthine | + | + |
| Hypoxanthine | + | + |
| Tyrosine | + | + |
| Adenine | − | − |
| Esculin | − | − |
| Gelatin | + | + |
| Starch | + | + |

TABLE III-continued

PHYSIOLOGICAL REACTIONS

|  | 31F508 | S. viridodiastaticus |
|---|---|---|
| Production of: | | |
| Urease | + | − |
| Melanin | − | − |
| Phosphatase | + | + |
| Decarboxylation of: | | |
| Acetate | + | + |
| Benzoate | − | − |
| Citrate | + | + |
| Lactate | + | ± |
| Malate | + | + |
| Mucate | − | − |
| Oxalate | + | − |
| Proprionate | + | + |
| Pyruvate | + | + |
| Succinate | + | + |
| Tartrate | − | − |
| Acid Production from: | | |
| Arabinose | − | + |
| Dulcitol | − | − |
| Erythritol | − | − |
| Glucose | + | + |
| Inositl | + | + |
| Lactose | + | + |
| Mannitol | + | + |
| Mannose | + | + |
| Methyl-α-D-glucoside | + | + |
| Melibiose | + | + |
| Raffinose | ± | − |
| α-L-Rhamnose | + | + |
| Sorbitol | − | − |
| Trehalose | + | + |
| Resistance to Lysozyme | − | − |
| Growth at | | |
| 22° C. | + | + |
| 28° C. | + | + |
| 45° C. | − | + |
| 50° C. | − | + |
| Growth on NaCl | | |
| 5% | + | + |
| 6% | + | ± |
| 8% | + | ± |

+: positive, −: negative, ±: weak

It is to be understood that for production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actinophages and the like.

The in vitro antibacterial activity of $31F508\alpha_1$ and $\alpha_2$ is determined against a spectrum of gram-positive and gram-negative bacteria by a standard agar dilution method. Mueller-Hinton agar with and without 5% sheep blood and two-fold decreasing concentrations of either $31F508\alpha_1$ or $\alpha_2$ are poured into petri dishes. The agar surfaces are inoculated with 1 to $5 \times 10^4$ colony forming units of bacteria by means of the Steers replicating units of bacteria by means of the Steers replicating device. The lowest concentration of antibiotic that inhibits growth of a bacterial strain after 18 hours incubation is recorded as the minimal inhibitory concentration for that strain. The results are given in Table IV. The results are given in Table V with sheeps blood added to the agar.

TABLE IV

In vitro Antibacterial Activity of $31F508\alpha_1$ and $31F508\alpha_2$

| Organism | Minimum Inhibitory Concentration mcg/ml | |
|---|---|---|
| | $31F508\alpha_1$ | $31F508\alpha_2$ |
| 1. Staphylococcus aureus (MEMC-89-4) | 0.030 | 0.004 |
| 2. Staphylococcus aureus (ID-2371) | 0.030 | 0.004 |
| 3. Staphylococcus aureus (ID-2727) | 0.008 | 0.002 |
| 4. Staphylococcus aureus (SMITH) | 0.004 | 0.002 |
| 5. Staphylococcus aureus (ID-3105) | 0.030 | 0.004 |
| 6. Staphylococcus aureus (ID-4379) | 0.030 | 0.004 |
| 7. Staphylococcus aureus (ATCC 29213) | 0.060 | 0.008 |
| 8. Staphylococcus haemolyticus (ID-4061) | 0.008 | 0.002 |
| 9. CNS (ID-3135) | 0.015 | 0.002 |
| 10. CNS (ID-3276) | 0.008 | 0.002 |
| 11. CNS (ID-3120) | 0.015 | 0.002 |
| 12. CNS (ID-3941) | 0.030 | 0.002 |
| 13. CNS (4615) | 0.015 | 0.002 |
| 14. E. faecalis (ID-4168) | 0.060 | 0.120 |
| 15. E. faecalis (ID-1829) | 0.120 | 0.060 |
| 16. E. faecalis (ID-2131) | 0.120 | 0.250 |
| 17. E. faecalis (12201) | 0.030 | 0.015 |
| 18. E. faecalis (ATCC 29212) | 0.060 | 0.060 |
| 19. E. faecium (12202) | 0.030 | 0.015 |
| 20. E. faecium (ID-3301) | 0.060 | 0.120 |
| 21. E. faecium (ID-4133) | 0.002 | 0.002 |
| 22. E. Avium (ID-3953) | 0.060 | 0.030 |
| 23. S. Pyogenes (ID-3187) | 0.002 | 0.002 |
| 24. S. agalactiae (ID-4079) | 0.004 | 0.004 |
| 25. Streptococcus pneumoniae (ID-4444) | 0.002 | 0.002 |
| 26. P. aeruginosa (ATCC 27853) | 2.000 | 2.000 |
| 27. M. morganii (VGH 84-11) | 1.000 | 0.500 |
| 28. E. coli (J2175) | 1.000 | 1.000 |
| 29. E. coli (J2445) | 0.060 | 0.004 |
| 30. E. coli (ATCC 25922) | 1.000 | 0.500 |
| 31. B. cereus (Bacto) | 0.500 | 0.250 |
| 32. S. lutea (ATCC 9341) | 0.002 | 0.002 |

TABLE V

In vitro Antibacterial Activity of $31F508\alpha_1$ and $31F508\alpha_2$ In the Presence of Sheeps Blood

| Organism | Minimum Inhibitory Concentration mcg/ml | |
|---|---|---|
| | $31F508\alpha_1$ | $31F508\beta_2$ |
| 1. Staphylococcus aureus (MEMC-89-4) | 0.060 | 0.060 |
| 2. Staphylococcus aureus (ID-2371) | 0.060 | 0.030 |
| 3. Staphylococcus aureus (ID-2727) | 0.015 | 0.015 |
| 4. Staphylococcus aureus (SMITH) | 0.008 | 0.002 |
| 5. Staphylococcus aureus (ID-3105) | 0.060 | 0.060 |
| 6. Staphylococcus aureus (ID-4379) | 0.120 | 0.060 |
| 7. Staphylococcus aureus (ATCC 29213) | 0.120 | 0.060 |
| 8. Staphylococcus haemolyticus (ID-4061) | 0.015 | 0.004 |

TABLE V-continued

In vitro Antibacterial Activity of
31F508α₁ and 31F508α₂
In the Presence of Sheeps Blood

| Organism | Minimum Inhibitory Concentration mcg/ml | |
|---|---|---|
| | 31F508α₁ | 31F508β₂ |
| 9. CNS (ID-3135) | 0.030 | 0.015 |
| 10. CNS (ID-3276) | 0.030 | 0.015 |
| 11. CNS (ID-3120) | 0.030 | 0.030 |
| 12. CNS (ID-3941) | 0.060 | 0.015 |
| 13. CNS (4615) | 0.030 | 0.015 |
| 14. *E. faecalis* (ID-4168) | 0.120 | 0.500 |
| 15. *E. faecalis* (ID-1829) | 0.500 | 0.500 |
| 16. *E. faecalis* (ID-2131) | 0.250 | 0.500 |
| 17. *E. faecalis* (12201) | 0.06 | 0.120 |
| 18. *E. faecalis* (ATCC 29212) | 0.120 | 0.500 |
| 19. *E. faecium* (12202) | 0.250 | 0.250 |
| 20. *E. faecium* (ID-3301) | 0.120 | 0.500 |
| 21. *E. faecium* (ID-4133) | 0.002 | 0.002 |
| 22. *E. Avium* (ID-3953) | 0.250 | 0.500 |
| 23. *S. Pyogenes* (ID-3187) | 0.004 | 0.030 |
| 24. *S. agalactiae* (ID-4079) | 0.015 | 0.015 |
| 25. *Streptococcus pneumoniae* (ID-4444) | 0.008 | 0.002 |
| 26. *P. aeruginosa* (ATCC 27853) | 2.000 | 4.000 |
| 27. *M. morganii* (VGH 84-11) | 2.000 | 2.000 |
| 28. *E. coli* (J2175) | 2.000 | 2.000 |
| 29. *E. coli* (J2445) | 0.120 | 0.030 |
| 30. *E. coli* (ATCC 25922) | 1.000 | 1.000 |
| 31. *B. cereus* (Bacto) | 1.000 | 1.000 |
| 32. *S. lutea* (ATCC 9341) | 0.002 | 0.002 |

The in vivo antibacterial activity of antibiotic 31F508α₂ is established by infecting female CD-1 mice from Charles River Laboratories, weighing 20+₋₂ g each, intraperitoneally of sufficient bacterial cells suspended in either broth or 5% hog gastric mucin to kill non-treated controls within 24–48 hours. Two-fold serially diluted doses of the antibacterial agent contained in phosphate buffered saline (PBS, pH 7.4, 0.01M) are administered intravenously (0.2 ml) or contained in 0.2% aqueous agar, subcutaneously (0.5 ml) or orally (0.5 ml) one half hour after infection. In each test, five mice are treated per dose level. The results of this test appear in Table VI.

TABLE VI

In vivo Activity of 31F508α₂
Against *Escherichia coli*#311

| Route | Dose Levels (Mg/Kg) | Survival Ratios |
|---|---|---|
| SSC | 8 | 0/5 |
| | 4 | 0/5 |
| | 2 | 0/5 |
| | 1 | 0/5 |
| | 0.5 | 0/5 |
| | 0.25 | 0/5 |
| SOD | 8 | 0/5 |
| | 4 | 0/5 |
| | 2 | 0/5 |
| | 1 | 0/5 |
| | 0.5 | 0/5 |
| | 0.25 | 0/5 |
| SIV | 4 | 0/5 |
| | 2 | 0/5 |
| | 1 | 0/5 |
| | 0.5 | 0/5 |
| | 0.25 | 0/5 |

In therapeutic use, the compounds of this invention may be administered in the form of conventional pharmaceutical compositions appropriate for the intended use. Such compositions may be formulated so as to be suitable for oral, parenteral or topical administration. The active ingredient may be combined in admixture with a non-toxic pharmaceutically acceptable carrier, which carrier may take a wide variety of forms depending on the form of preparation desired for administration, i.e., oral, parenteral or topical.

GENERAL FERMENTATION CONDITIONS

Cultivation of *Streptomyces viridodiastaticus* subsp. "*littus*". 31F508 may be carried out in a wide variety of liquid culture media. Media which are useful for the production of 31F508 include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

GENERAL PROCEDURE FOR THE ISOLATION OF 31F508α₁, 31F508α₂, 31F508β₁ and 31F508β₂

The 31F508α₁, 31F508α₂, 31F508β₁ and 31F508β₂ are recovered from the fermentation broth at pH6, mixing with toluene, filtering through a filter press, washing the press with water, loading the aqueous filtrate and washes onto an HP-20 column, eluting the column with 90% methyl alcohol-water and concentrating the methyl alcohol-water giving a crude product.

The crude product is then separated into the α₁, α₂, β₁ and β₂ components and further purified by high performance liquid chromatography on a reverse-phase column equilibrated with 0.1% trifluoroacetic acid in water followed by elution with an acetonitrile gradient to 10%. Active fractions are pooled and freeze dried. Freeze dried fractions are dissolved in 0.01M hydrochloric acid, applied to a reverse phase column and eluted with an acetonitrile gradient to 10% resolves the two components α₁ and α₂. In neutral or basic solution, α₁ and α₂ convert to the beta form. Beta is the quinone form of α₁ or α₂ having lost hydrogens from the oxygens connected to carbon-10 and 13.

The invention will be further described in conjunction with the following non-limiting examples.

EXAMPLE 1

Inoculum Preparation

A typical medium used to grow the primary inoculum is prepared according to the following formula:

| | |
|---|---|
| Glucose | 1.0% |
| Dextrin | 2.0% |
| Yeast extract | 0.5% |
| NZ Amine A ®[1] | 0.5% |
| Mississippi line | 0.1% |
| FD-82 defoamer | 0.3% |
| Water qs | 100.0% |

[1][A pancreatic digest of casein, registered trademark of Sheffield Chemical, Norwich, NY]

This medium is sterilized and 100 ml, in a 500 ml flask, is inoculated with *Streptomyces viridodiastaticus* subsp. *"littus"*. The medium is then placed on a rotary shaker and incubated at 28° C. for 48 hours providing a primary inoculum. This primary inoculum is then used to inoculate 10 liters of the same sterile medium in a bottle. This medium is grown at 28° C. for 72 hours with a sterile air flow of 10 liters per liter of mash per minute and agitation by an impeller driven at 500 rpm, providing a tertiary inoculum.

EXAMPLE 2

Fermentation

A fermentation medium of the following formulation is prepared:

| | |
|---|---|
| Glucose | 1.0% |
| Dextrin | 2.0% |
| Yeast extract | 0.5% |
| NZ Amine A ®[1] | 0.5% |
| Mississippi line | 0.1% |
| FD-82 defoamer | 0.3% |
| Water qs | 100.0% |

[1][A pancreatic digest of casein, registered trademark of Sheffield Chemical, Norwich, NY]

This medium is sterilized and 1500 liters is then inoculated with the tertiary inoculum of Example 1. The fermentation is conducted at 28° C. with a sterile air flow of 200 liters per minute and agitation by an impeller driven at 200 rpm for 50 hours, at which time the mash is harvested.

EXAMPLE 3

Isolation and Purification of 31F508$\alpha_1$, 31F508$\alpha_2$ and 31F508$\beta$ The mash is mixed with 7.1 liters of toluene for 30 minutes and filtered through a 36 inch filter press. The press cake is washed with water. The aqueous filtrate and washes are loaded onto a 60L HP20 column. After water washing with two column volumes, the column is eluted with three column volumes of 90% methyl alcohol-water. Twenty liter fractions are taken and assayed. Active fractions are pooled, concentrated and freeze dried. The HP20 column is washed with two column volumes of methyl alcohol. The wash is concentrated to about 3 liters.

The freeze dried material is suspended in methanol and the insolubles removed by filtration. The soluble material is concentrated to dryness and the concentrate dissolved in 1% trifluoroacetic acid in water. Insolubles are removed by centrifugation. The soluble material is loaded onto a preparative reverse phase $C_{18}$ column equilibrated with 0.1% trifluoroacetic acid in water. The column is eluted with an acetonitrile gradient to 10%. Active fractions containing the alpha component are pooled and freeze dried. Active fractions containing the beta component are adjusted to pH 8 with solid ammonium bicarbonate and extracted with methylene chloride. The beta component is stored in methylene chloride as drying leads to rapid decomposition.

The freeze dried material is dissolved in 0.01M hydrochloric acid and applied to a PRP-1 reversed phase column. The column is eluted with an acetonitrile gradient to 10% affording two components $\alpha_1$ and $\alpha_2$. The fractions are freeze dried to off white powders. The total of $\alpha_1$ isolated is 20 mg. The total of $\alpha_2$ isolated is 350 mg. In neutral or basic solution, $\alpha_1$ and $\alpha_2$ converts to the beta form. Beta is the quinone form of $\alpha_1$ or $\alpha_2$ having lost hydrogens from the oxygens connected to carbon-10 and 13.

What is claimed is:

1. A biologically pure culture of the microorganism *Streptomyces viridodiastaticus* subsp. *"littus"* having the deposit accession number NRRL-21082N said culture being capable of producing antibiotics 31F508$\alpha_1$, 31F508$\alpha_2$, 31F508$\beta_1$ and 31F508$\beta_2$, upon fermentation in an aqueous nutrient medium containing assimilable sources of carbon, nitrogen and inorganic anion and cation salts.

* * * * *